US00PP25095P3

(12) United States Plant Patent
Sheehan

(10) Patent No.: US PP25,095 P3
(45) Date of Patent: Nov. 25, 2014

(54) GRAPEVINE NAMED 'SHEEGENE-18'

(50) Latin Name: *Vitis vinifera*
Varietal Denomination: Sheegene-18

(75) Inventors: Timothy P. Sheehan, Vancouver, WA (US); Mary Ann Sheehan, legal representative, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 0 days.

(21) Appl. No.: 13/506,245

(22) Filed: Apr. 6, 2012

(65) Prior Publication Data

US 2013/0269072 P1 Oct. 10, 2013

(51) Int. Cl.
*A01H 5/00* (2006.01)

(52) U.S. Cl.
USPC ..... Plt./207

(58) Field of Classification Search
USPC ..... Plt./205, 207
See application file for complete search history.

*Primary Examiner* — Anne Grunberg
(74) *Attorney, Agent, or Firm* — Baker Manock & Jensen, PC; Eric C. Cole

(57) ABSTRACT

A new and distinct variety of grapevine characterized by the production of medium, green-colored seedless grapes that mature in early September when grown in the San Joaquin Valley of Central California. The grapes of this new variety are produced on strong woody stems and branches and are well adapted to commercial handling.

1 Drawing Sheet

Latin name of the genius and species of the plant claimed: The claimed plant relates to a new and distinct variety of *Vitis vinifera* to be known as 'Sheegene-18'.

CROSS REFERENCE TO RELATED APPLICATIONS

The claimed plant is not subject of a related application.

STATEMENT OF ANY FEDERALLY-SPONSORED RESEARCH AND DEVELOPMENT

The claimed plant is not subject of Federally-sponsored research or development.

VARIETY DENOMINATION

The new variety of *Vitis vinifera* is the result of hybridization of 'Princess' (unpatented), the pollen parent, and 'Red Globe' (U.S. Plant Pat. No. 4,787), the seed parent. The new variety was first hybridized by Timothy P. Sheehan in the Spring of 2000. The new variety was asexually propagated in the dormant season of 2003, grafted on virus-free rootstock in a *Vitis vinifera* variety block located near East of Fowler, Calif. The new variety was planted as rooted cuttings in the dormant season of 2007 in a *Vitis vinifera* variety block located north and west of Delano, Calif. The new variety produces a medium, green-colored seedless grape with very good flavor. The new variety has been shown to maintain its distinguishing characteristics through asexual propagation.

The new variety is distinguished from its pollen parent, 'Princess' (unpatented), in that the new variety produces green-colored seedless grapes, as compared to the white-colored seedless grapes produced by its pollen parent, 'Princess' (unpatented). The new variety is distinguished from its seed parent, 'Red Globe'(U.S. Plant Pat. No. 4,787), in that the new variety produces medium sized green-colored seedless grapes, as, compared to its seed parent, 'Red Globe'(U.S. Plant Pat. No. 4,787), that produces exceptionally large red-colored seeded grapes.

BACKGROUND OF THE INVENTION

The present invention relates to a new and distinct variety of grapevine that produces a medium, green-colored seedless grape that matures during early September when grown in the San Joaquin Valley of Central California.

SUMMARY OF THE INVENTION

The 'Sheegene-18' grapevine is characterized by producing a medium, green-colored seedless grape that has very good flavor and it is productive and mature for harvesting and shipment in early September when grown in the San Joaquin Valley of Central California. The new variety can be compared to 'Thompson Seedless' (unpatented) but the grapes produced by the new variety mature four to five weeks later, among other distinguishing characteristics.

BRIEF DESCRIPTION OF THE DRAWINGS

The accompanying drawing is a color photograph that shows several mature leaves across the top portion of the photograph with an immature leaf in the middle, just below the leaves are two small clusters of mature grapes and one large cluster of mature grapes, just below the clusters of grapes are several grapes cut longitudinally and horizontally displaying the heart and pulp, just below the cut grapes are tendril leaves, and on both sides of the photograph are mature branches with one immature branch located on the left side of the photograph.

DETAILED BOTANICAL DESCRIPTION

Referring more to the horticultural description of the new and distinct variety of grapevine, the following has been observed under the ecological conditions prevailing at the origin vineyard located near Delano, Calif., in the San Joaquin Valley of Central California. All major color descriptions are by reference to the Dictionary of Color by Maerz & Paul, First Edition, published in 1930. Common colors names are also used in several instances.

Vine:

*Size*.—Medium.
*Vigor*.—Very good.
*Chilling requirements*.—Normal for grapevines in the lower San Joaquin Valley of Central California.
*Figure*.—With wide cordons forming a "T" shape.
*Productive capacity*.—Very good.
*Regularity of bearing*.—Regular.

Trunk:

*Size*.—Medium; 7 inches [17.78 cm] in circumference, 17 inches [43.18 cm] above ground (5 year old wood).
*Surface texture*.—Rough and shaggy.
*Color of bark*.—P1.4 H9 Liver Brown Autumn Oak+(5 year old wood).
*Mature cane color*.—P1.21 L6-Parrot green (8 to 12 month old wood).
*Nodes*.—Two on cane.
*Length between nodes*.—6.5 to 9 inches [16.51 to 22.86 cm].
*Shoot length*.—6 inches [15.24 cm].
*Shoot shape* (*habit*).—Slender.
*Shoot habit*.—Droopy.
*Tendrils number/location*.—Single at node.
*Tendrils length*.—4.5 to 5.5 inches [11.43 to 13.97 cm].
*Tendrils form*.—Bifurcate.
*Bud shape*.—Triangular.
*Bud size*.—Small; 0.039 to 0.079 inches [1 to 2 mm].

Branches:

*Size*.—Medium; 2 inches [5.08 cm] in circumference.
*Cordons*.—37 inches [93.98 cm] on one side of trunk ; 42.99 inches [109.20 cm] on the other side of trunk.
*Surface texture*.—Slightly rough with grooves.
*Color* (*one year or older branches*).—P1.15 J7 Light reddish.
*Color* (*immature branches*).—P1.15 J7 Light reddish (Upper side); P1.20 L6 Piquant green (Lower side).

Leaves:

*Size*.—Medium to large.
*Density*.—Dense.
*Average length*.—4.75 to 5.75 inches [12.07 to 14.61 cm].
*Average width*.—4.13 to 6.5 inches [10.49 to 16.51 cm].
*Form*.—Pentagonal.
*Texture* (*upper surface*).—Smooth.
*Texture* (*lower surface*).—Glabrous.
*Leaf vein color*.—P1.20 K1 Russet gr.
*Margin form*.—Slightly undulate.
*Leaf margin*.—Toothed.
*Leaf vein thickness*.—0.08 inches [2 mm].
*Stem glands*.—None.
*Petiole size*.—Moderate.
*Petiole length*.—5 inches [12.70 cm].
*Petiole color* (*lower surface*.—P1.6 I7 Near slate U.
*Petiole color* (*upper surface*).—P1.17 L8 Novo gr.
*Stem glands*.—None.
*Lobes* (*average*).—Five.
*Stipules*.—None.
*Tooth size*.—0.16 to 0.28 inches [4 to 7 mm] in width; 0.20 to 0.28 inches [5 to 7 mm] in length.
*Tooth number*.—7 to 14 per lobe.
*Tooth shape*.—Triangular.

Inflorescence:

*Size*.—4.72 to 8.27 inches [12 to 21 cm] in length.
*Number per vine*.—Prolific; up to sixty-four clusters.

Flowers:

*Flower buds*.—0.04 to 0.08 inches [1 to 2 mm].
*Flower buds surface texture*.—Glabrous.
*Date of bloom*.—May 8.
*Date of full bloom*.—May 14.
*Size* (*average*).—0.20 inches [5 mm].
*Petal sinus form*.—Upside-down "U" shape.
*Petals* (*color*).—P1.7 C8 Mauve Taupe.
*Petals* (*size*).—0.16 inches [4 mm].
*Pistil color*.—P1.17 L8 Nova gr.
*Date of visible berry set*.—May 14.
*Size of berries*.—0.08 inches [2 mm] when fruit first set.

Fruit:

*Solids*.—19.1 Brix.
*Acids*.—0.42.
*Sugar/acid ratio*.—57.8.
*Juice pH*.—4.01.
*Seeds*.—None.
*Rudimentary seed structures*.—One to two.
*Capstem pedicel*.—0.39 inches [10 mm].
*Berry weight*.—53.86 grams (1.90 oz).
*Juice color*.—P1.20 L2 Oasis.
*Cluster size*.—Large.
*Cluster average length* (*not including stem*).—7 inches [17.78 cm].
*Cluster average diameter*.—5.50 inches [13.97 cm].
*Cluster density*.—Compact.
*Cluster form*.—Conical.
*Stem*.—Generally large.
*Stem caliper*.—0.12 inches [3 mm].
*Berry size*.—Medium.
*Berry form*.—Ovate.
*Berry numbers* (*average*).—75 berries per bunch.
*Berry size* (*average dimension along longitudinal axis*) .—0.88 inches [2.24 cm].
*Berry size* (*average dimension along transverse axis*).—0.94 inches [2.40 cm].

Skin:

*Skin*.—Thickness: Medium.
*Texture*.—Semi-tough.
*Ground color*.—P1.19 L4 Light green.
*Pulp color*.—P1.21 B3 Courge gr.

Flesh:

*Flesh color*.—P1.18 L6 Love Bird.
*Juice production*.—Good.
*Flavor*.—Very good.
*Aroma*.—Mild.
*Texture*.—Firm.
*Eating quality*.—Very good.
*Resistance to disease*.—Unknown.
*Harvesting*.—Early September in the San Joaquin Valley of Central California.
*Shipping and handling qualities*.—Very good.

Having thus described and illustrated our new variety of grapevine, we claim:

1. A new and distinct variety of grapevine, substantially as described and illustrated herein, characterized principally by its production of medium, green-colored seedless grapes that mature four to five weeks after 'Thompson Seedless' (unpatented) which it resembles.

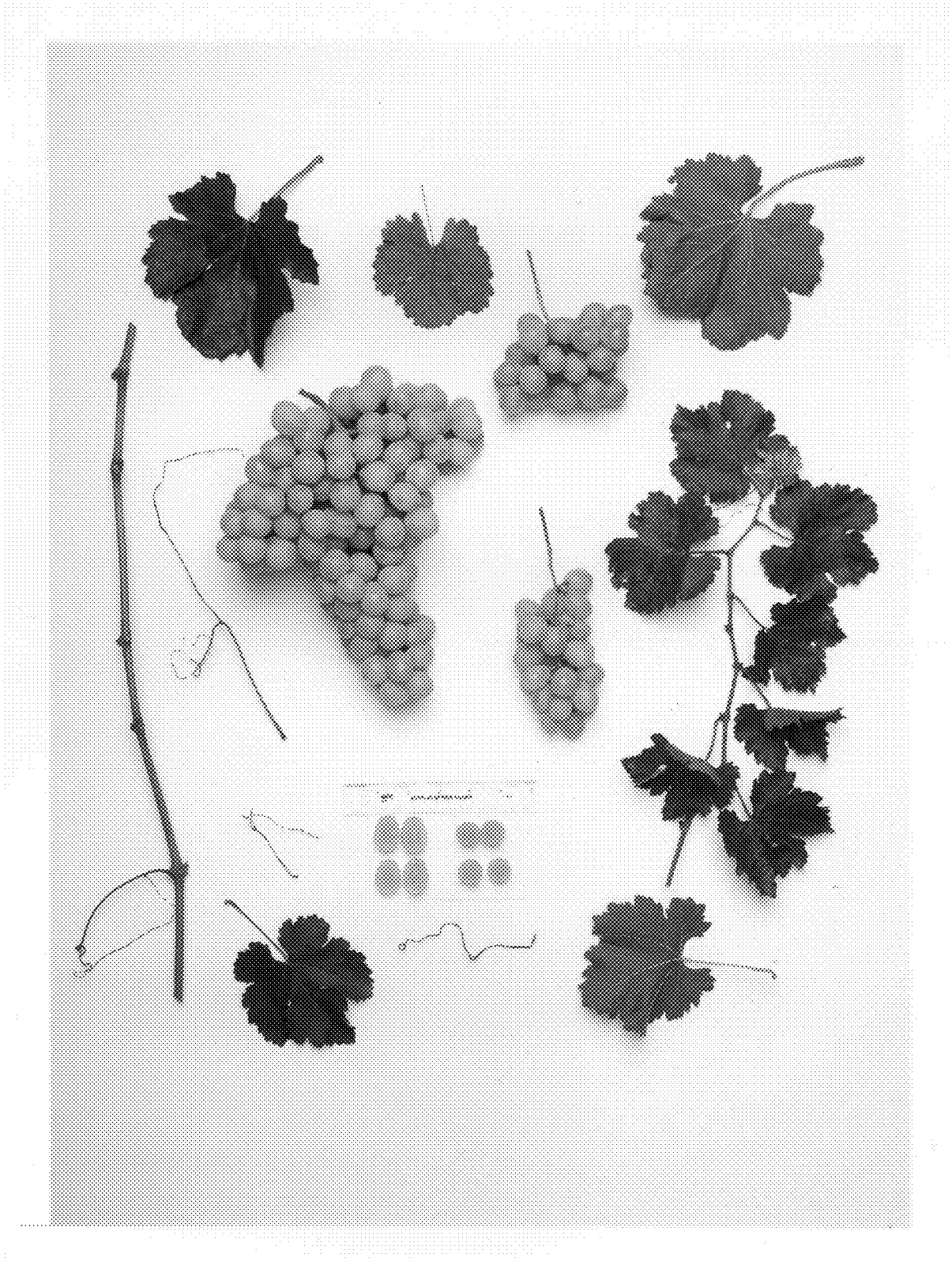

* * * * *